United States Patent [19]
Wilson et al.

[11] 4,316,115
[45] Feb. 16, 1982

[54] POLYMERIC PIEZOELECTRIC MICROPROBE WITH DAMPER

[75] Inventors: David T. Wilson, Billerica; Roger H. Tancrell, Cambridge; Joseph Callerame, Lexington, all of Mass.

[73] Assignee: Raytheon Company, Lexington, Mass.

[21] Appl. No.: 99,438

[22] Filed: Dec. 3, 1979

[51] Int. Cl.³ .................................. H01L 41/08
[52] U.S. Cl. .................... 310/327; 310/334; 310/800
[58] Field of Search .................. 310/334–337, 310/327, 224, 800; 228/663

[56] References Cited

U.S. PATENT DOCUMENTS

| | | | |
|---|---|---|---|
| 3,553,501 | 1/1971 | Thill | 310/327 |
| 3,794,866 | 2/1974 | McElroy et al. | 310/327 |
| 3,798,473 | 3/1974 | Murayama | 310/800 X |
| 3,832,580 | 8/1974 | Yamamuro et al. | 310/800 X |
| 3,855,847 | 12/1974 | Leschek | 310/334 X |
| 3,921,442 | 11/1975 | Soloway | 310/336 X |
| 3,925,692 | 12/1975 | Leschek et al. | 310/327 |

Primary Examiner—Mark O. Budd
Attorney, Agent, or Firm—V. D. Pitruzzella; J. D. Pannone; M. D. Bartlett

[57] ABSTRACT

A probe detects sonic energy in liquids and in materials containing liquids such as the flesh of living beings, the probe being particularly adapted for medical ultrasonics. The probe is constructed of materials having acoustic impedances substantially equal to that of water to maximize the transfer of sonic energy in a living being to an electric signal within the probe for accurate detection of high frequency pulses having a duration less than a microsecond. A piezoelectric polymer serves as the transducer and is mounted at the end of the probe housing between a thin metallic window which serves as one electrode, and a metallized rubber rod which serves as the second electrode and sonically insulates the transducer from the housing. An acoustically absorbent ring affixed to the perimeter of the face of the probe, and a flaring of the back end of the probe, reduce the diffraction and reflection of acoustic waves for improved accuracy in the measurement of submicrosecond pulses.

15 Claims, 7 Drawing Figures

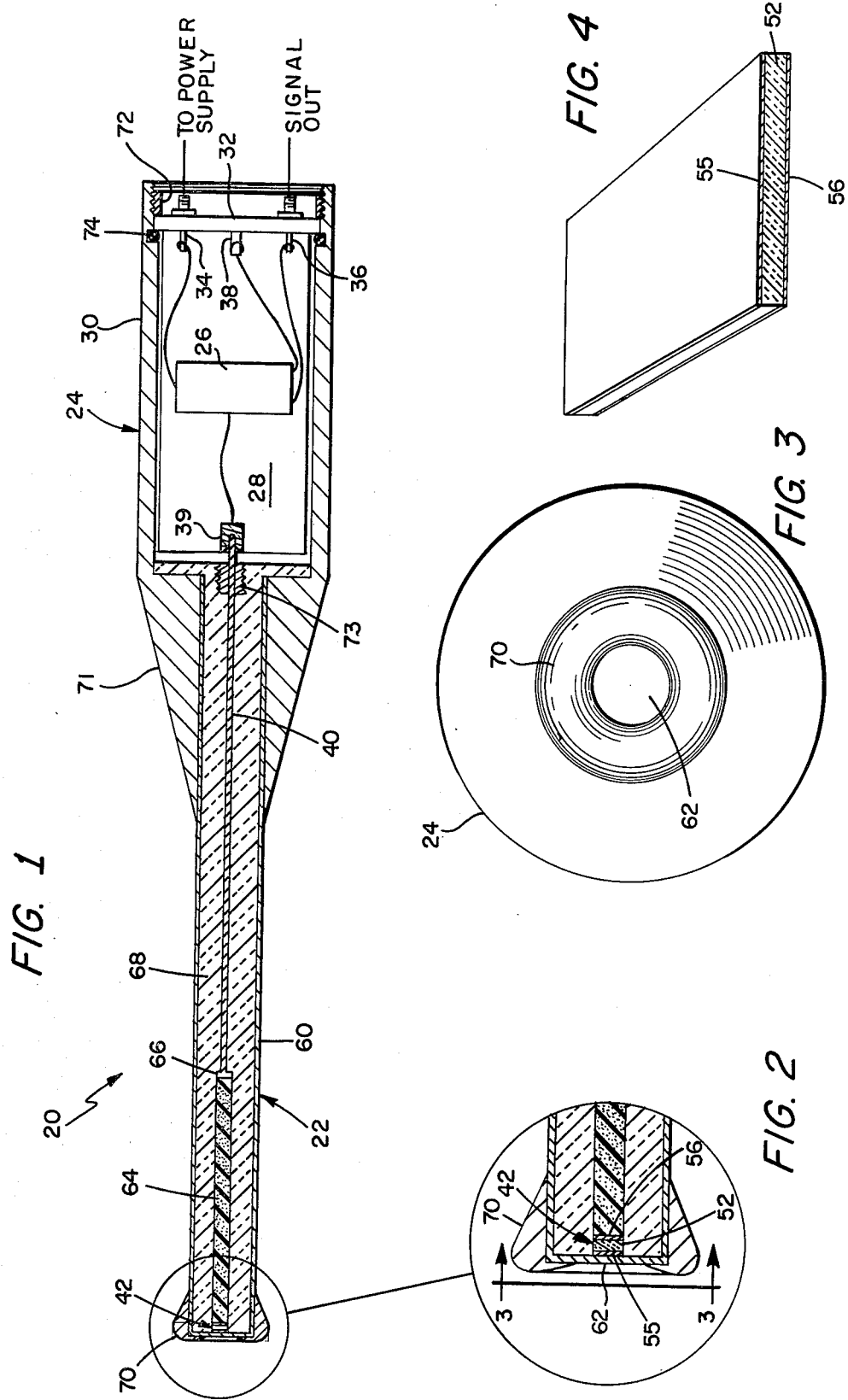

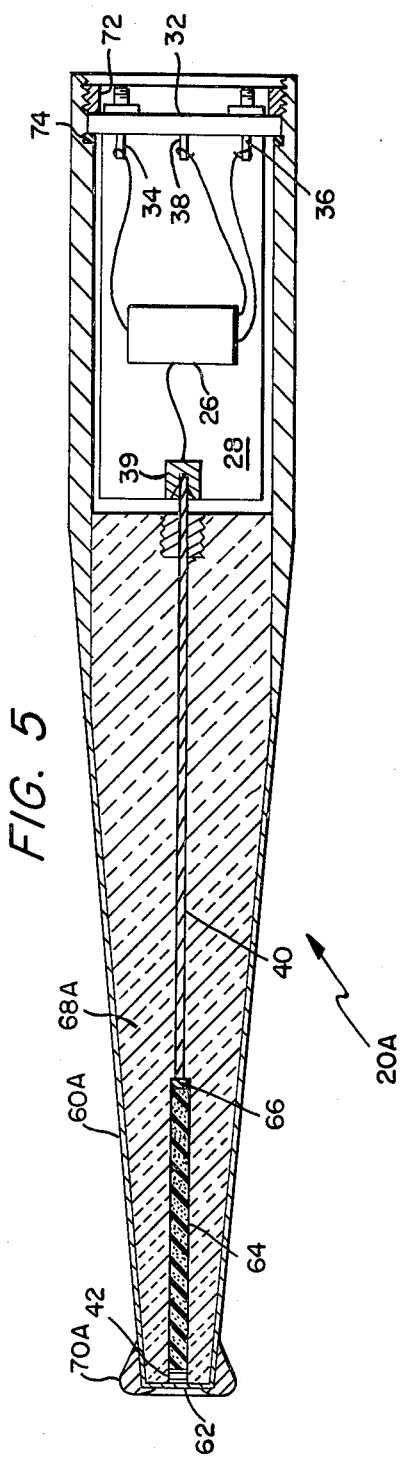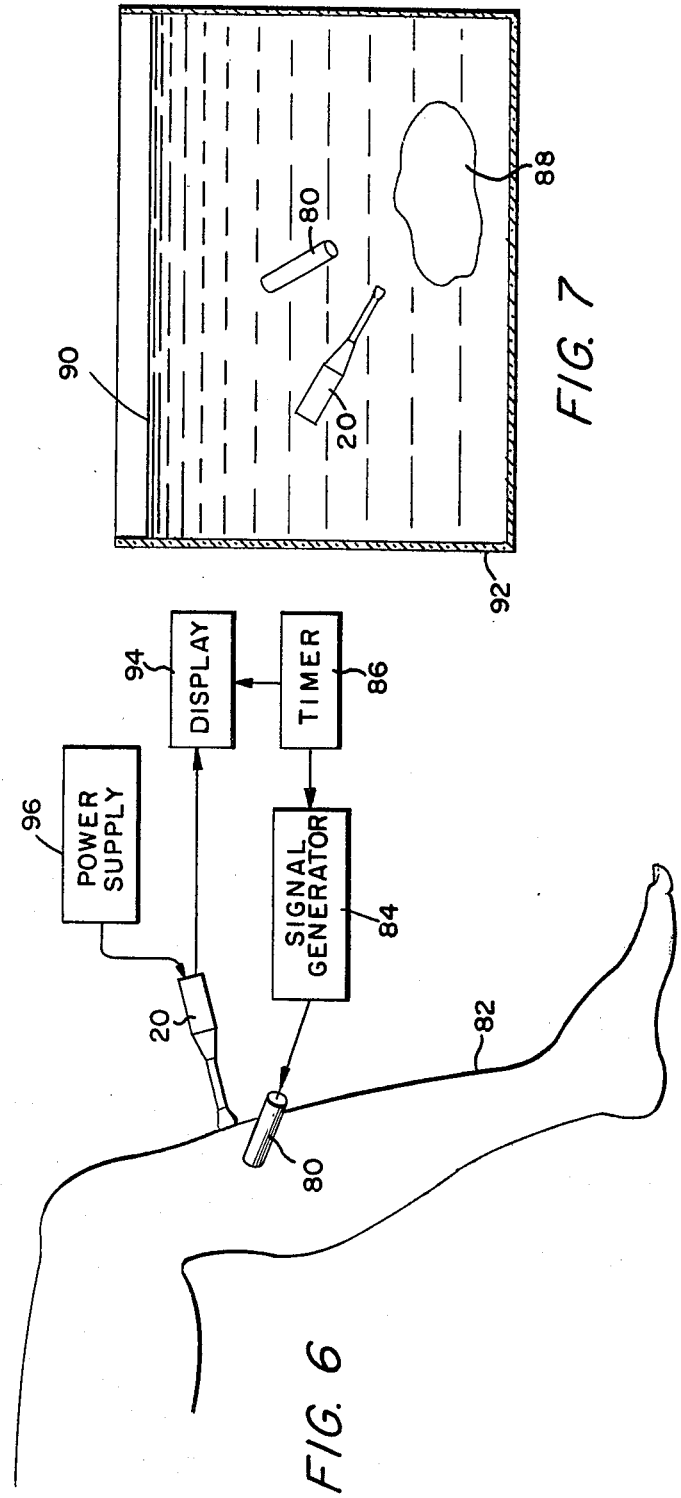

POLYMERIC PIEZOELECTRIC MICROPROBE WITH DAMPER

BACKGROUND OF THE INVENTION

This invention relates to sonar transducers and, more particularly, to a transducer probe assembly adapted for detection of short pulses of high frequency sonic energy as is utilized in medical ultrasonics.

Transducers for the conversion of sonic energy into electrical signals are employed aboard ships for the detection of underwater sounds, and also in probes for the detection of sounds propagating within the tissues of living beings. The transducers are generally reciprocal devices in that electrical signals applied to the transducers are converted into sound waves which can propagate within the ocean and within living tissues.

In the past, transducers have generally been constructed of a piezoelectric ceramic material such as lead-zirconatetitanate (PZT). PZT is relatively dense as compared to water and has a much higher acoustic impedance than does water. In sonar applications, the transducer has generally been mounted in strong metallic casings with relatively heavy weights mechanically coupled to the transducer in order to provide a measure of impedance matching between the impedances of the transducer and of the water. Probes employing smaller quantities of PZT and utilizing reduced weight of the impedance matching structures have been employed in medical ultrasonic research for the observation of sound waves within living tissues. However, such probes have not been completely satisfactory due to the large difference of impedance between the transducer and the living tissue, the living tissue having an acoustic impedance substantially equal to that of water. The large difference of impedance has reduced the efficiency of conversion of sonic energy to electric energy thereby reducing the sensitivity of the probe. Furthermore, the ceramic materials utilized in transducers, in combination with their mechanical acoustic matching structures, provide a structure which is sufficiently resonant acoustically to inhibit the measurement of sonic pulses of relatively short durations, less than a microsecond duration, as are advantageously utilized in medical ultrasonics.

With a view towards providing transducers which are capable of receiving the foregoing submicrosecond sonic signals with minimal distortion, consideration has been given to a material, other than the ceramics, which has piezoelectric properties and an acoustic impedance more nearly equal to that of water than is the impedance of the ceramics. One such material, polyvinylidene fluoride is commercially available from the Penwalt Corporation of King of Prussia, Pa. and EMI Limited, Middlesex, England. However, this polymeric material is presently obtainable only in thin films, typically 30 microns thick. The films are produced with metallized layers on the top and the bottom surfaces by a deposition of, typically, aluminum on the surfaces. A problem arises in that the physical structures which have been utilized in the fabrication of sonar transducers employing the relatively massive, rugged ceramic materials do not admit the use of the relatively light, fragile polymeric film.

SUMMARY OF THE INVENTION

The aforementioned problems are overcome and other advantages are provided by a transducer probe which is capable of receiving acoustic signals propagating in liquid media and living tissues wherein the acoustic signals include frequencies ranging up to one megahertz (MHz) and even higher frequencies with signal durations as short as a fractional microsecond interval. In accordance with the invention, the probe is provided with a transducer element formed of a piezoelectric material having an acoustic impedance substantially equal to that of water, and having metallization on the surfaces of the material for applying electric signals to the material. Due to the substantial equality of impedance of the transducer element with the impedance of water, the transducer element may be viewed as being transparent to acoustic energy. The probe is preferably immersed fully in water for detecting sounds propagating in the water, the acoustic transparency minimizing interference of the transducer element to the propagation of sonic waves to permit observation of submicrosecond sonic pulses.

In a preferred embodiment of the invention, the transducer element is formed of a film of a polymeric piezoelectric material such as polyvinylidene fluoride. The probe is formed with an elongated cylindrical or frustoconical housing terminated by an acoustic window. The housing is typically fabricated of stainless steel to prevent a development of corrosion from liquids in which the probe may be immersed. The window is fabricated of a material which is substantially lossless to acoustic energy, and to further insure against acoustic losses, is fabricated with a thickness which should be less than approximately ten percent of the wavelength of the acoustic energy propagating through the window. In the preferred embodiment of the invention, a window thickness of less than one percent of the wavelength has been utilized. The window has been fabricated of stainless steel in a thickness of 0.025 millimeter (mm) since the stainless steel is sufficiently strong to permit the fabrication of such a thin window and for providing acoustical conductivity through the window. In addition, the electrical conductivity of the stainless steel provides for electrical shielding of the transducer.

The transducer element is placed in physical contact with the window so that the window and the housing serve as an electrical contact for the transducer element. A second electrical contact is made by means of an electrically conducting sonic insulator. The sonic insulator is, preferably, a rubber rod for attenuating any sonic reverberations which might otherwise be induced within the housing. The rubber rod is formulated with metal particles to provide an electrical conductivity thereto, the rubber rod abutting the transducer element to secure it against the window while the electrical conductivity enables the rod to serve as the second electrical contact for the transducer element. The cylinder of insulating material, such as a phenolic material, surrounds the rubber rod to serve as a spacer element and to provide electrical insulation between the rod and the housing. A cylinder of insulating material also serves as an acoustic insulator to further attenuate any sonic reverberations which might otherwise develop within the housing. Any voids between the transducer element, the rod, and the insulating cylinder, are filled with oil to insure an acoustic transmission path which is free of resonance effects associated with an air pocket. An acoustically absorbent ring affixed to the perimeter of the face of the probe, and a flaring of the back end of the probe, reduce the diffraction and reflection of acoustic waves for improved accuracy in the measurement of submicrosecond pulses.

BRIEF DESCRIPTION OF THE DRAWINGS

The aforementioned aspects and other features of the invention are explained in the following description taken in connection with the accompanying drawings wherein:

FIG. 1 is a sectional view of an acoustic probe constructed in accordance with the invention;

FIG. 2 is an enlarged view of a face of the probe of FIG. 1 designated by an encircled region in FIG. 1;

FIG. 3 is an end view of the probe of FIG. 1 taken along the lines 3—3 of FIG. 2;

FIG. 4 shows a portion of a polymer film with metallized layers thereon which is utilized in forming the transducer element seen in FIGS. 1 and 2;

FIG. 5 is an alternative embodiment of the invention wherein the housing as provided with a frusto-conical shape for reducing sonic reverberations within the housing; and for reducing electrical capacitance between an electrically conducting rubber rod and the housing;

FIG. 6 shows a sonic echo system utilizing a conventional sound transmitter and the probe of FIG. 1 for portraying an image of the internal structure of living tissues;

FIG. 7 is an alternative arrangement of the sound transmitter and probe of FIG. 6 wherein the transmitter and the probe are immersed in a liquid for imaging an object submerged within the liquid.

DESCRIPTION OF THE PREFERRED EMBODIMENT

Referring now to FIGS. 1, 2 and 3, an acoustic probe 20 which is constructed in accordance with the invention is seen to comprise a cylindrically shaped neck 22 and a pod 24 secured to the end of the neck 22, the neck 22 housing the acoustic sensing elements while the pod 24 houses the elements of an electrical amplifier 26. The amplifier 26, which is of conventional design, for low noise figure, is shown diagrammatically and is seen to be mounted on a circuit board 28 which is enclosed by a housing 30 of the pod 24. The board 28 is secured to a cover 32 of the housing 30 to facilitate the making of electrical connections between the amplifier 26 and the following terminals, namely, a terminal 34 which is a coaxial cable connector for the supplying of power to the amplifier 26, a terminal 36 which is a coaxial cable connector for providing the output signal of the amplifier 26, and a grounding terminal 38. The terminals 34, 36 and 38 are mounted on the cover 32. A socket 39 is coupled to the amplifier 26 and is secured to the board 28 for slidably mating with a terminal 40 which is coupled to a transducer element 42 as will be described hereinafter.

Referring also to FIG. 4, the transducer element 42 is fabricated in the form of a thin circular disc by cutting out a disc from a piezoelectric polymeric film 52, such as polyvinylidene fluoride having metallized layers 55–56 thereon. The layers 55 and 56 are formed by the deposition of a metal, such as aluminum or gold upon the front and back surfaces of the film 52. The transducer element 42 has been constructed with a diameter of 1.5 mm in one embodiment of the invention, the film 52 having a thickness of 30 microns. The layers 55 and 56 are utilized for detecting an electric field which is generated within the film 52 in response to sound waves incident thereupon. While a film 52 having the aforementioned 30 micron thickness has been utilized in constructing the probe 20, it is believed that a thicker film would provide a greater efficiency in the conversion of sonic energy to electrical signals. With the use of piezoelectric polymer of greater thickness, the relatively thin disc shape of the transducer element 42 would have a thicker shape such as that of a tile. Also, it is noted that, while the transducer element 42 has been fabricated with a circular shape, the transducer element 42 may alternatively be fabricated of a square shaped tile.

A feature of the invention is the mounting of the transducer element 42 within a housing 60 of the neck 22 wherein the neck housing 60 provides both isolation from radio-frequency interference and sonic reverberations. The neck housing 60 is formed of a tubular section of an electrically conducting material, such as stainless steel, and is terminated at its front end with a window 62 which is constructed of an electrically conductive material which is resistant to corrosion and transmissive of sonic energy. In the preferred embodiment of the invention, the window 62 has been constructed of stainless steel since stainless steel, as has been noted hereinabove, is sufficiently strong to permit the fabrication of the window 62 with a thickness of 0.025 mm, this thickness being less than one percent of a wavelength of the sound which is to be detected by the probe 20. Since stainless steel is propagative of sonic energy, and since the thickness is substantially less than the sonic wavelength, sound waves can propagate through the window 62 with essentially no reflection or attenuation, even though the acoustic impedance of bulk stainless steel, many wavelengths in thickness, is many times greater than that of water.

The acoustic impedance of the transducer element 42 closely approximates that of water so that, upon the contacting of the window with living tissue or a body of water as will be seen in FIGS. 6 and 7, sonic energy is able to propagate through the transducer element 42 with substantially no reflection therefrom, the transducer element 42 being essentially transparent to the sonic energy. The metallized layers 55 and 56 have substantially less thickness than that of the film 52 and of the window 62 so as to appear essentially transparent to the sonic energy. As seen in FIG. 3, the transducer element 42 is placed in the front end of the neck 22 in contact with a back surface of the window 62 so that sonic energy can readily propagate through the window 62 and into the transducer element 42. In addition, the contacting of the transducer element 42 with the window 62 provides for a path of electrical conduction wherein the neck housing 60 and the window 62 with the front layer 55 provide an electrode for the transducer element 42.

A second electrode for the transducer 42 is provided by a rod 64 which is electrically coupled between the terminal 40 and the back layer 56 of the transducer element 42. The rod 64 is constructed of electrically conductive, sound absorbing material such as rubber which has been impregnated with metal particles. A disc 66 on the front end of the terminal 40 mates with the back end of the rod 64 to insure electrical conduction between the rod 64 and the terminal 40. The terminal 40 is conveniently fabricated of a copper wire. The rubber of the rod 64 has an acoustic impedance with a magnitude similar to that of the acoustic impedance of water so that the propagation of sonic energy from the transducer element 42 into the rod 64 is accomplished with a minimum of reflected energy thereby minimizing any ringing by the superposition of incident and reflected waves, and, thus, facilitating the observation of short-duration acoustic signals in the submicrosecond range.

A further feature of the invention is the enclosing of the transducer element 42 and the rod 64 and the terminal 40 by an acoustic absorber 68, the absorber 68 having been fabricated of a phenolic material in the preferred embodiment of the invention. It is noted that the diameter of the transducer element 42 is approximately equal to the length of two wavelengths of the sonic energy at a frequency of approximately two megahertz (MHz), which frequency is often utilized in ultrasonic research. As may be seen in FIG. 3, the diameter of the neck housing 60 is greater than that of the transducer element 42 with the result that the interior dimensions of the neck 22 are sufficiently large to admit the development of sonic reverberations in the absence of sound absorbing material such as that provided by the absorber 68 and the rod 64. Both the absorber 68 and the rod 64 absorb sonic energy, and thereby inhibit the formation of reverberations, while their acoustic impedances, which have a magnitude similar to that of water and of the transducer element 42, promotes the propagation of sonic energy through the transducer element 42 with a minimum of reflection. Thereby, sonic signals detected by the transducer element 42 are essentially free of the influence of reflection and reverberation with the result that the aforementioned short-duration pulses of sonic energy can be observed.

To further improve the response of the probe 20 to the short-duration pulses of sonic energy, a ring 70 of an acousticly absorbingly material, such as rubber, is provided around the periphery of the window 62. The ring 70 has a smooth tapered outer surface to inhibit the diffraction of an incoming sonic wave about the edges of the window 62. Also, the pod housing 30 is provided with a front section 71 having a frusto-conical shape with a cone angle of approximately 20° to 40°. The frusto-conical shape gives the probe 20 an increasing outer diameter which deflects sound waves, travelling parallel to and alongside the neck housing 60, away from the probe 20. Thereby, there is substantially no reflection of the sound waves off the discontinuity formed by the back end of the probe 20. It has been found that, with a probe constructed in accordance with the preferred embodiment of the invention, sonic pulse durations of less than a half wavelength of the carrier frequency of the sound wave can be observed.

With respect to the electrical connections between the transducer element 42 and the amplifier 26, it is noted that the pod housing 30 is formed of a metal for electrical conduction, such as stainless steel, and is secured to the back end of the neck housing 60 in a conventional manner as by brazing or by screw threads. Similarly, the cover 32 is fabricated of metal and is secured to the pod housing 30 by a threaded metallic retainer ring 72. Thus, the terminal 38 is electrically connected via the cover 32 and the pod housing 30 to the neck housing 60. Secure electrical contact between the disk 66 and the rod 64 is maintained by a center-bored screw 73 affixed to the terminal 40, the screw being threadedly secured to the back end of the absorber 68 for urging the disk 66 against the rod 64. Accordingly, the electrical conductors of the neck 22 are seen to be in a coaxial arrangement wherein the inner conductor is formed of the rod 64 and the terminal 40 while the outer conductor is formed of the housings 60 and 30. The absorber 68 thus serves as a dielectric spacer between the inner and the outer conductors.

In selecting a length of the rod 64, it is noted that increasing length of the rod 64 provides for increased attenuation of sonic reverberation, and also results in increased electric capacitance between the inner and outer conductors of the coaxial arrangement. While FIG. 1 shows a length of the rod 64 which is approximately one third the length of the neck housing 60, a longer length of the rod 64 may be utilized, for example, a length of the rod 64 equal to approximately two thirds the length of the neck housing 60. While the shorter length of the rod 64 results in a somewhat reduced attenuation of sonic reverberations, since the terminal 40 has been found experimentally to contribute to the presence of the reverberations as does the neck housing 60, the reduced length of the rod 64 provides the advantage of reduced capacitance between the inner and outer conductors with a resultant increase in the amplitude of the electric signal applied via the terminals 40 and 38 to the amplifier 26. A still further reduction in capacitance results by a reduction in the length of the neck housing 60.

In the assembly of the components of the probe 20, it is noted that a petroleum based oil, such as SAE 30 weight oil, has been placed along the interfaces between the transducer element 42, the window 62, the rod 64 and the absorber 68 for filling any voids along the interfaces which would otherwise be air pockets which tend to be resonant and introduce acoustic discontinuities with attendant reverberations. The insertion of the oil into such voids removes such resonances and reverberations. The interior of the pod housing 30 is also filled with the oil. After insertion of the transducer element 42, the rod 64, and the terminal 40, the absorber 68 is then inserted via the pod 24 into the neck 22 in the space between the rod 64 and the neck housing 60. The circuit board 28 having the amplifier 26 thereon and attached to the cover 32, is then inserted into the pod 24 and positioned by the cover 32. An O-ring 74 is placed between the cover 32 and a shelf of the pod housing 30, the O-ring 74 and the oil within the pod housing 30 serving to prevent the entry of water or other contaminents into the pod 24 when the probe 20 is immersed as will be seen in FIG. 7. The retainer ring 72 tightens the cover 32 against the O-ring 74. Upon insertion of the circuit board 28 into the pod 24, the socket 39 slidably mates with the terminal 40 to electrically connect the amplifier 26 with the transducer element 42.

Referring now to FIG. 5, there is seen an alternative embodiment of the probe 20 of FIGS. 1–3, the embodiment of FIG. 5 being identified as the probe 20A. The transducer element 42 and the window 62 are the same as that shown in FIG. 1. Similarly, the amplifier 26 and the electrical connections made thereto are the same as that shown in FIG. 1. In FIG. 5, improved immunity to reverberations is attained by modifying the cylindrical shape of the neck housing 60 of FIG. 3 to become a frusto-conical shaped housing 60A in FIG. 5. Similarly, the outer cylindrical surface of the absorber 68 of FIG. 3 has assumed a frusto-conical shape in the absorber 68A of FIG. 5. The ring 70 of FIG. 3 has been similarly modified to provide the ring 70A of FIG. 5 which mates with the housing 60A of FIG. 5. The the rod 64 and the terminal 40 appear in the same form in the embodiments of both FIGS. 3 and 5. The reduced reverberations are believed to be obtained by virtue of the fact that a sonic wave impinging upon the interior wall of the housing 60A in FIG. 5 is reflected in a direction generally along the axis of the probe 20A for attenuating the sound in the absorber 68A. An additional feature of the embodiment of FIG. 5 is found in the increasing separation between the rod 64 and the housing 60A with progression along the axis of the probe 20A towards the amplifier 26, the increasing separation providing for an increasing diminution in the magnitude of the electrical capacitance with a resultant increase in the magnitude of an electrical signal coupled from the transducer element 42 to the amplifier 26.

Referring now to FIGS. 6 and 7, there is seen a system for sonic range finding and imaging. In FIG. 6, there is shown one arrangement using the probe 20 and a transmitting transducer 80 for imaging living tissue such as that of a human leg 82. A signal generator 84, in response to clock pulses of a timer 86 provides electrical signals which are converted by the transducer 80 to sound waves which propagate into the leg 82. The transducer 80 and the probe 20 contact the leg 82 to provide a good acoustic path between the transmitter 80 and the leg 82, and between the probe 20 and the leg 82. If desired, the face of the probe 20 and of the transmitter 80 may be coated with a gel to insure that there are no air pockets, or voids, between the faces of the probe 20 and the transducer 80.

A preferred arrangement for the use of the probe 20 and the transmitting transducer 80 is shown in FIG. 7 wherein a subject 88 which is to be imaged is submerged within a liquid, such as water 90 enclosed within a container 92. Good acoustical contact between the water and the probe 20 and the transducer 80 are obtained by emersing the complete probe 20 and the face of the transducer 80 into the water 90. To minimize the effect on the received sonic signal of interference with sound waves reflected from the surface of the water and the walls of the container 92, the probe 20 is spaced at a distance, thirty centimeters having been found to be sufficient, from the water surface and the walls of the container 92. Echoes obtained from material within the leg 82, or from material within the subject 88, are reflected back through the probe 20 to be presented on a display 94. The timer 86 provides clock pulse signals to the display 94 so that the difference in times between the transmission and reception of the sonic signal appear as a measurement of depth of reflecting surfaces within the leg 82 or the subject 88. The terminal 36 (seen in FIG. 3) of the probe 20 is coupled to the display 94 while the terminal 34 of the probe 20 is coupled to a power supply 96 for powering the amplifier 26 of FIG. 3 to amplify the echoes received by the probe 20.

In constructing the preferred embodiment, the rod 64 is formed of a silicone rubber which is absorbent of acoustic energy, the rod 64 has a diameter of 1.5 millimeter (mm) and a length of 22 mm, the rod being available from Chomerics of Woburn, Mass. The absorber 68 is 75 mm long and 5.5 mm in diameter, and is fabricated of a linen phenolic material. Terminal 40 is a copper rod of 1.0 mm diameter, the rod extending a distance of 75 mm. The stainless steel tube of the neck housing 60 has an outer diameter of approximately 60 mm, and 0.25 mm wall thickness. The cylindrical portion of the pod housing 30 has a length of 38 mm, while the flared portion is 25 mm in length as measured along the axis of the probe 20. The outer diameter of the pod 24 is 18 mm.

Returning to FIG. 4, it is noted by way of alternative embodiments, that other piezoelectric polymeric material having an acoustic impedance similar to that of water may be utilized since such materials would be essentially transparent to the propagation of sonic energy as is the polyvinylidene fluoride, also known as polyvinylidene difluoride due to the two fluorine atoms in each monomer. For example, a plastic film, known commercially as Mylar, may be utilized, the film being metallized to serve as the electrodes. The reverberation inhibiting structure of the rod 64, the absorber 68 and the ring 70 of FIG. 1 in combination with the acoustically transparent window 62 and the elongated neck housing 60 is applicable to a transducer element which is transparent to sonic energy coupled from water, or material of similar acoustic impedance, into the transducer element.

It is understood that the above described embodiments of the invention are illustrative only and that modifications thereof may occur to those skilled in the art. Accordingly, it is desired that this invention is not to be limited to the embodiments disclosed herein but is to be limited only as defined by the appended claims.

What is claimed is:

1. A transducer assembly comprising:
   a polymeric piezoelectric element having front and back surfaces thereof;
   an elongated housing enclosing said piezoelectric element and having a substantially transparent acoustic window at an end thereof in contact with said first surface of said piezoelectric element;
   an elongated sound absorbing member in contact with said second surface of said piezoelectric element;
   a spacer member disposed circumferentially around said sound absorbing member and located between said sound absorbing member and said housing, said piezoelectric element having an acoustic impedance substantially equal in magnitude to the impedance of a medium to which said transducer assembly is acoustically coupled for the detection of sonic signals propagating in said medium; and
   means for isolating said polymeric piezoelectric element from sound waves diffracted from the edge of said acoustic window.

2. A transducer assembly according to claim 1 wherein said sound absorber and said spacer member are fabricated of materials which attenuate sound waves substantially, said materials having acoustic impedances which are substantially equal in magnitude to the impedance of said polymeric piezoelectric element.

3. A transducer assembly according to claim 2 wherein said sound absorber is electrically conductive for conducting an electrical signal to a terminal of said transducer element, and wherein said housing is electrically conducting for conducting electrical signals to another terminal of said piezoelectric element.

4. A transducer assembly according to claim 1 further comprising:
   means for substantially eliminating reflections of sound waves from the exterior of said housing.

5. A transducer assembly according to claim 4 wherein:
   said reflection eliminating means comprise an outwardly flaring portion of said housing.

6. A transducer assembly according to claim 1 wherein: said isolating means comprise an acoustically absorbing element disposed along the periphery of said acoustic window.

7. A transducer assembly according to claim 2 wherein: said sound absorbing member comprises a metallized resilient rod.

8. A transducer assembly according to claim 3 further comprising: an amplifier disposed in close proximity and electrically coupled to said polymeric piezoelectric element.

9. A transducer assembly according to claim 3 wherein: the relative dimensions of said electrically conductive sound absorbing member, said spacer member and said housing reduce the electrical capacitance of said assembly.

10. A transducer assembly comprising:
a piezoelectric element comprising a polymerized film having front and back surfaces thereof, there being front and back metallized films deposited, respectively, on said front and said back surfaces of said polymerized film;
a housing enclosing said piezoelectric element and having a window in contact with said first surface of said piezoelectric element, said window being electrically conductive and transmissive of sonic energy, said window serving as a first electrical terminal for said piezoelectric element;
a sound absorbing member in contact with said second metallized film, said sound absorbing member being electrically conductive and serving as a second electrical terminal for said piezoelectric element; and
an amplifier disposed within said housing and electrically coupled to said polymerized film.

11. A transducer assembly according to claim 6 wherein said sound absorbing member comprises a metallized rubber rod for securing said polymerized film against said window.

12. A transducer assembly according to claim 6 further comprising:
means for reducing the electrical capacitance between said housing and said sound absorbing member.

13. A transducer assembly according to claim 12 wherein:
said capacitance reducing means comprise an electrically insulating spacer member of sound absorbing material, said spacer member being located between said electrically conductive sound absorbing member and said housing.

14. A transducer assembly according to claim 6 further comprising:
a sound absorbing ring member disposed along the periphery of said window.

15. A transducer assembly according to claim 12 wherein: said polymerized film has a size of the order of a wavelength of the sonic energy used.

* * * * *

UNITED STATES PATENT OFFICE
CERTIFICATE OF CORRECTION

Patent No. 4,316,115          Dated February 16, 1982

Inventor(s) David T. Wilson et al

It is certified that error appears in the above-identified patent and that said Letters Patent are hereby corrected as shown below:

Column 4, Line 61: change "disc" to --disk--;

Column 6, Line 44: change "contaminents" to --contaminants--;

Column 6, Line 65: delete "the" (third occurrence);

Column 7, Line 34: change "emersing" to --immersing--;

Column 10, Line 5: Claim 11 - change "according to claim 6" to --according to claim 10--;

Column 10, Line 9: Claim 12 - change "according to claim 6" to --according to claim 10--;

Column 10, Line 21: Claim 14 - change "according to claim 6" to --according to claim 10--.

Signed and Sealed this

Eleventh Day of May 1982

[SEAL]

Attest:

Attesting Officer

GERALD J. MOSSINGHOFF
Commissioner of Patents and Trademarks